(12) United States Patent
Montalban

(10) Patent No.: US 9,737,379 B2
(45) Date of Patent: Aug. 22, 2017

(54) RAPID PALATAL EXPANDER AND METHOD FOR THE ASSEMBLY THEREOF

(71) Applicant: VISOTTICA INDUSTRIE S.p.A., Susegana (TV) (IT)

(72) Inventor: Rinaldo Montalban, Venezla (IT)

(73) Assignee: VISOTTICA INDUSTRIE S.p.A., Susegana (IT)

( * ) Notice: Subject to any disclaimer, the term of this patent is extended or adjusted under 35 U.S.C. 154(b) by 0 days.

(21) Appl. No.: 14/876,833

(22) Filed: Oct. 7, 2015

(65) Prior Publication Data
US 2016/0022382 A1   Jan. 28, 2016

Related U.S. Application Data

(63) Continuation of application No. 13/943,830, filed on Jul. 17, 2013, now abandoned.

(51) Int. Cl.
*A61C 3/00* (2006.01)
*A61C 7/10* (2006.01)

(52) U.S. Cl.
CPC ........... *A61C 7/10* (2013.01); *Y10T 29/49568* (2015.01)

(58) Field of Classification Search
CPC .... A61C 7/06; A61C 7/10; A61C 7/36; Y10T 29/49568
See application file for complete search history.

(56) References Cited

U.S. PATENT DOCUMENTS

| 4,354,832 | A | * | 10/1982 | Wallshein | A61C 7/10 254/98 |
|---|---|---|---|---|---|
| 4,482,318 | A | | 11/1984 | Forster | |
| 4,571,177 | A | * | 2/1986 | Dahan | A61C 7/10 433/7 |
| 5,281,133 | A | | 1/1994 | Farzin-Nia | |
| 5,439,377 | A | | 8/1995 | Milanovich | |
| 6,309,213 | B1 | * | 10/2001 | Forster | A61C 7/10 433/7 |
| 6,644,967 | B2 | | 11/2003 | Ceppatelli et al. | |
| 2004/0152033 | A1 | | 8/2004 | Collins | |
| 2007/0218416 | A1 | * | 9/2007 | Keles | A61C 7/10 433/7 |
| 2007/0275341 | A1 | | 11/2007 | Hanks | |

FOREIGN PATENT DOCUMENTS

| DE | 102007002040 A1 | 7/2008 |
|---|---|---|
| EP | 0308645 A1 | 3/1989 |
| EP | 1247498 A1 | 9/2002 |
| WO | 03/071976 A1 | 9/2003 |
| WO | 2012/042547 A1 | 4/2012 |
| WO | 2012/120477 A1 | 9/2012 |

* cited by examiner

*Primary Examiner* — Heidi M Eide
(74) *Attorney, Agent, or Firm* — Mark M. Friedman

(57) ABSTRACT

Rapid palatal expander made of a first and a second main body (5, 6) provided with aligned female threads (7, 8) that are engaged by the threaded stems (4) of an actuator element (2). This actuator element (2) is provided with a drive head (3) from which the stems (4) extend in opposite directions and aligned with opposite threads. Following the rotation of the drive head (2) the main bodies (5, 6) move parallel to the longitudinal extension direction Y of the actuator element (2). During the movement the main bodies (5, 6) are guided by a first and a second pair of rods (11, 12), which are fixed in a single body with the first and the second main body (5, 6), respectively, and are slidably mutually engaged with each other.

6 Claims, 15 Drawing Sheets

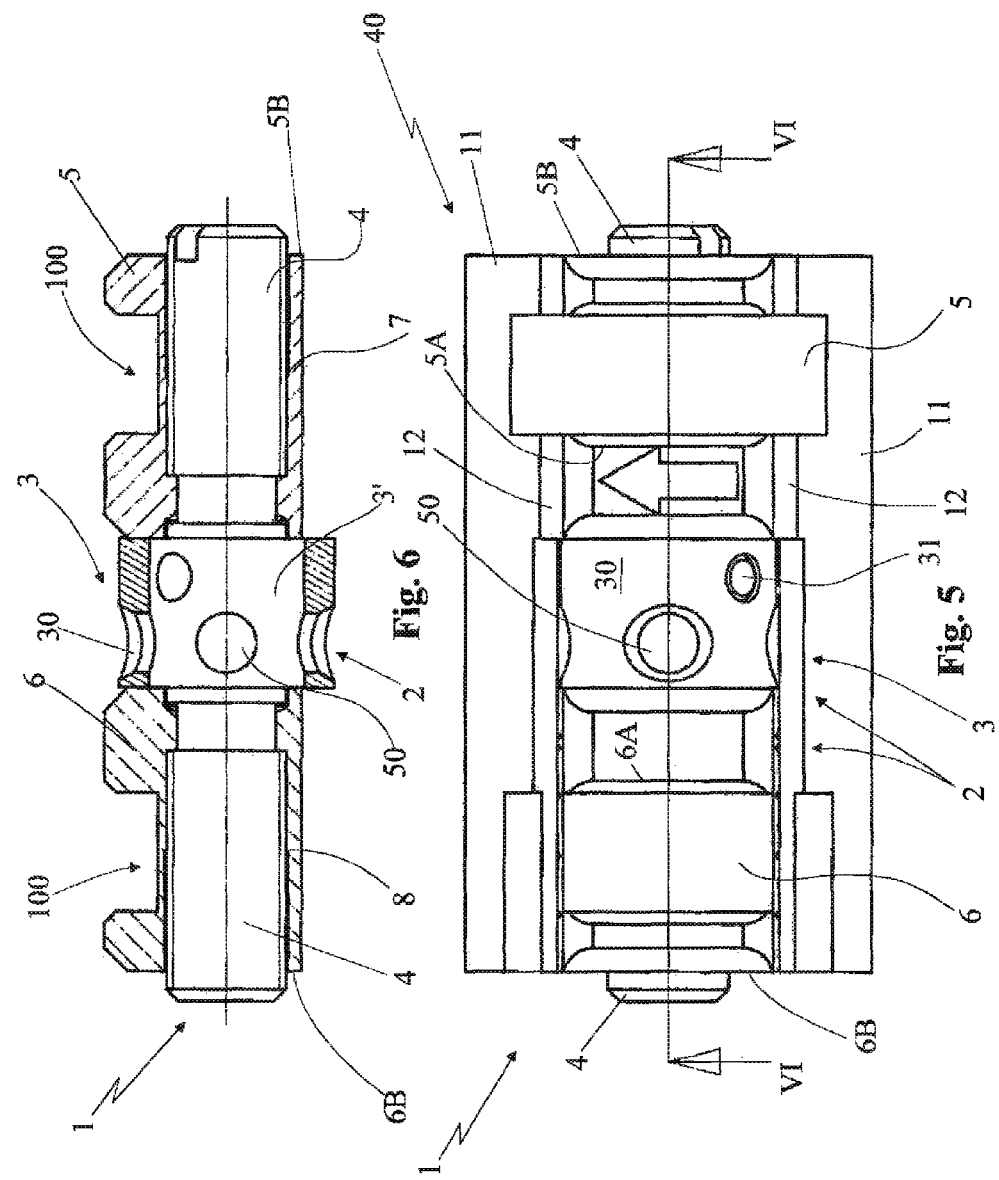

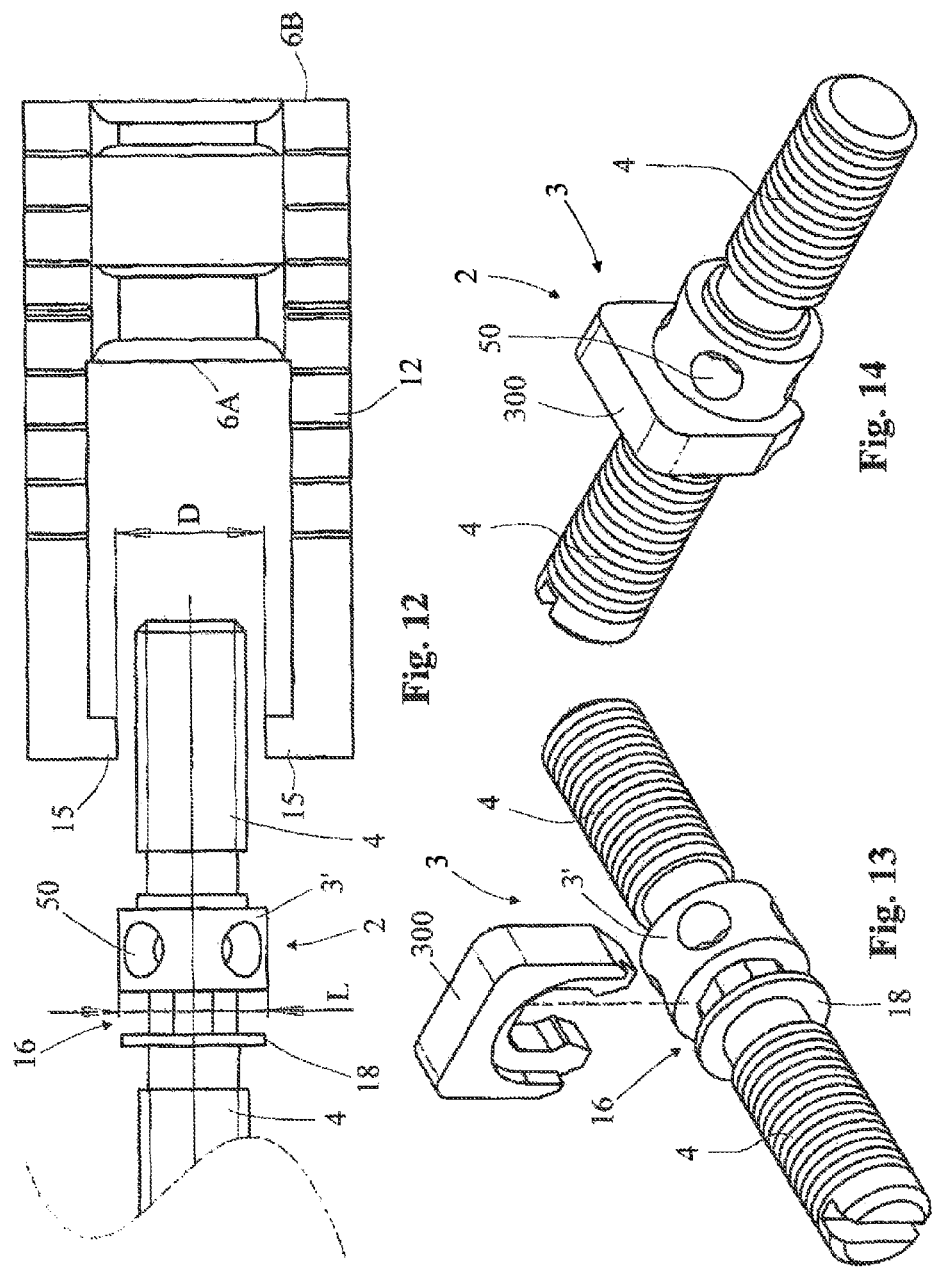

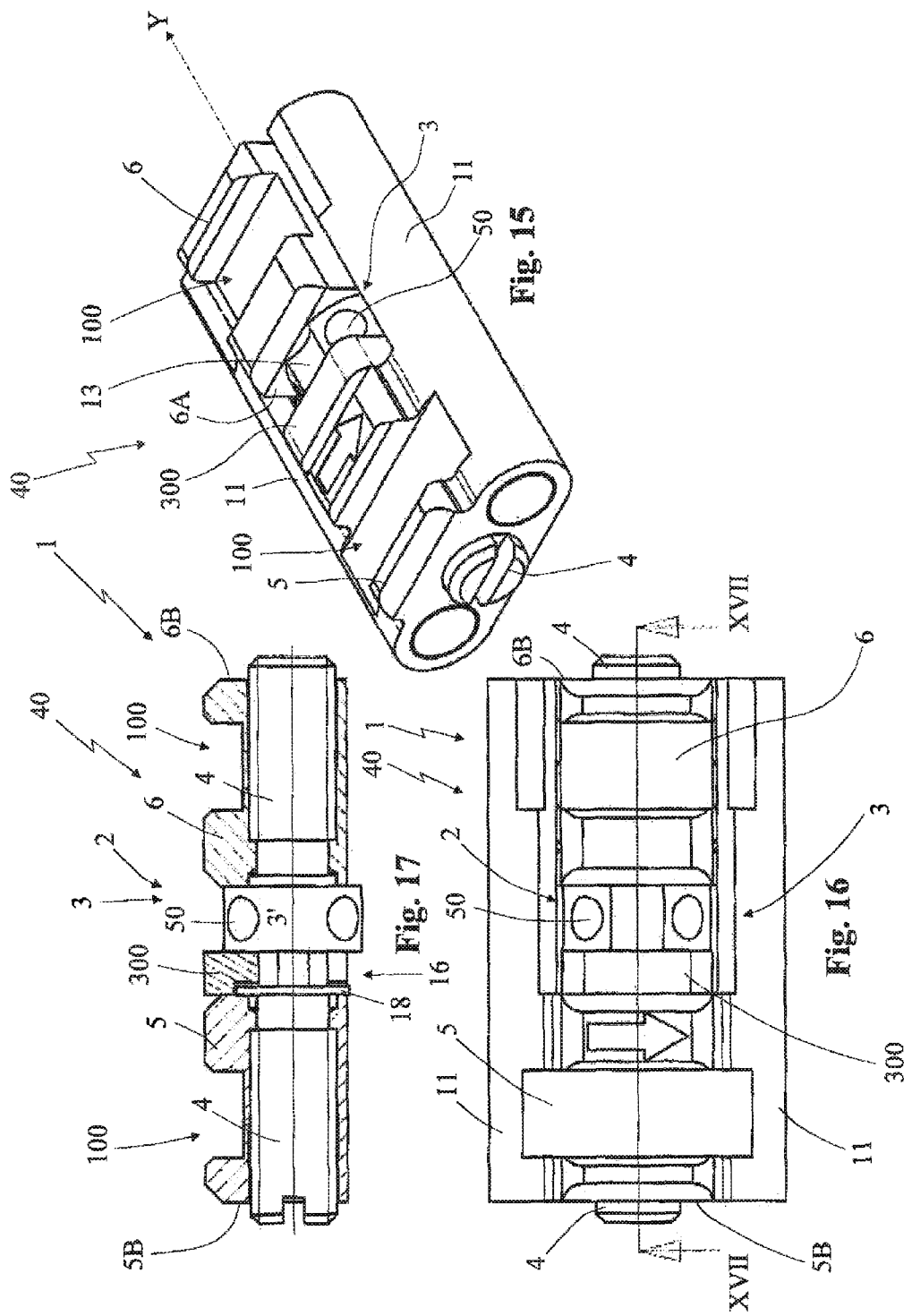

RAPID PALATAL EXPANDER AND METHOD FOR THE ASSEMBLY THEREOF

FIELD OF APPLICATION

The present invention regards a rapid palatal expander and a method for the assembly thereof, according to the preamble of the respective independent claims.

The present rapid palatal expander, otherwise termed expander or spreader in the technical jargon of the field, is advantageously intended to be employed in the orthodontics field for the treatment of cases of skeletal hypoplasia of the upper jaw, especially for subjects during development, before the end of puberty, when the median suture of the palate is not yet completely ossified.

It is an instrument that is applied in the mouth for a period of time and which causes the mechanical widening of the palate in a manner so as to create more space between the two rows of the upper dental arch.

The rapid palatal expander is therefore an orthodontics instruments and more generally a dental-maxillo-facial aid employable for the correction of a pathological condition of transverse growth deficit of the upper jaw, which can involve a poor dental occlusion, and can also have repercussions on phonesis, deglutition as well as respiration.

Therefore, the rapid palatal expander, object of the present invention, is inserted in the field of the orthodontic devices and the maxillo-facial devices.

STATE OF THE ART

Different mechanical solutions of rapid palatal expanders (with ERP initials) are known in the orthodontics field and have been for some time employed for the correction of the transverse growth deficit of the upper jaw. Such known expanders are based on the same mechanical principle of moving two bodies away from each other with the use of a screw engaged thereto, of twin and opposite thread type. More in detail, the palatal expanders of conventional type present on the market commonly have a support structure comprising:

two main bodies mechanically connected to two or more rigid arms which are extended in opposite directions, and are intended to interact, by means of anchorage bands (e.g. molar bands) or other mechanical elements, with corresponding opposite portions of the dental arch;

an elongated twin-screw actuator element provided with a drive head with cylindrical form arranged in a median position thereof, and with two stems with threads with opposite senses obtained, such stems extended aligned in opposite directions, starting from the drive head, until they are engaged in threaded seats of the two main bodies; the drive head is peripherally provided with holes for the insertion of a key adapted to allow the rotation of the twin-screw element for the mutual moving away or closer of the two main bodies and hence of the molar bands that act on the arch;

one or two guide pins, which are slidably inserted inside corresponding holes obtained in the two main bodies, in order to guide the translation of the latter following the driving in rotation of the twin-screw element.

In the orthodontics field, there is the particular need that the aforesaid rapid palatal expanders have a high rigidity. Indeed, possible clearances, even small ones present in the mutual moving away/closer of the two main bodies, are translated into considerable shifting at the terminations of the arms where the latter are connected to the molar bands, with the result that the palatal expander device is not very stable and unsuitable for precisely and adjustably transmitting the progressive expansion action on the teeth.

However, production and mounting requirements of the various components make it difficult to avoid the presence of clearances.

For example, from the patents WO-A-2012120447 and EP-A-1247498, rapid palatal expanders of the above-described type are known, which are produced by assembling together numerous components, each of which obtained with their own normal production tolerances. In particular, each guide pin slides with clearance in at least one hole of a main body, which is translated into a functioning that is not very fluid, with inefficient mechanical transmission at the terminations of the arms.

In addition, obtaining the expanders with a considerable number of components implies production times and costs that are clearly quite high.

Nor can the fixing with laser welding of the guide pins in the holes of one of the two main bodies, as provided for in one palatal expander embodiment described in the patent EP-A-1247498, be deemed satisfactory. Indeed, from the production standpoint, such expander requires a further step for positioning the pins and the laser fixing thereof in the holes of one of the main bodies. From the performance standpoint, the mechanical stability reached with such laser fixing still does not result satisfactory, given that the positioning of the welded pins cannot occur in a sufficiently precise manner and their clearance in the holes of the other main body still causes undesired shifting, i.e. even leads to small jams during the moving away or closer of the two main bodies of the palatal expander.

Also known from patent EP-A-0308645 is a palatal expander, in which the guide pins are obtained by means of two U-shaped plates, whose superimposed arms allow carrying the main bodies during the expansion in a guided manner. Neither does this embodiment allow reaching a high mechanical stability since the superimposed arms of the pins are engaged with each other only by means of facing flat surfaces in contact with each other, substantially unsuitable for creating a particularly stable mechanical constraint. Also the number of components employed for the production of the latter palatal expander of known type is rather high, and such to negatively affect the overall costs of the production process.

Also known are palatal expanders of less conventional type, in which the two main bodies assume the form of two shells, including an external fixed shell and an internal movable shell. The latter can be driven to translate in a guided manner inside the external fixed shell by means of an actuator element with screw having a single thread. The drive head is idly mounted on the external shell and engaged with the threaded stem with the internal shell. The external shell is provided with an opening for accessing the drive head with a key in order to rotate it. A first drawback of this palatal expander lies in the fact that by moving only one of the two shells, a double rotation is necessary, given the same thread pitch, in order to obtain a relative movement analogous to those of the abovementioned palatal expanders which engage a twin-screw actuator element.

A second drawback of such known expander lies in the high structural complexity mainly connected to the need to obtain processing on the external shell in order to precisely adapt it to the shape of the internal shell.

A limit of various rapid palatal expanders of known type also lies in the fact that they do not have an end stop that terminates the moving away of the two main bodies and prevents an accidental excessive separation of the same two main bodies from disengaging them from the thread of the twin-screw element, causing the breaking apart of the palatal expander in the mouth of the patient during the activation thereof.

The end stop of the palatal expanders is constrained by the form and by the bulk of the main bodies which must be stopped in their expansion travel.

Palatal spreaders of the above-described conventional type and provided with end stops in the opening are in any case known from the U.S. Pat. No. 4,482,318, for example. The latter describes a palatal expander, in which the two guide pins have enlarged ends with radially projecting edges, susceptible to abut against a shoulder obtained at the holes of the opposite main bodies when the same main bodies are moved away from each other in the position of their maximum expansion. Such solution has proven rather difficult to achieve, in particular since rather than providing for simple holes in the main bodies, shaped holes are provided i.e. equipped with shoulders in order to act as stops of the guide pins.

Presentation of the Invention

In this situation, the problem underlying the present invention is to eliminate the drawbacks of the abovementioned prior art by providing a rapid palatal expander which is provided with an improved mechanical stability, allowing the effective transmission, in the progressive adjustments thereof, of the pressure to the dental arch.

A further object of the present finding is to provide a rapid palatal expander which is structurally simple and entirely reliable in operation.

A further object of the present finding is to provide a rapid palatal expander which is simple and inexpensive to obtain.

A further object of the present finding is to provide a rapid palatal expander which is entirely safe for the patient who wears it, in particular without any risk for the patient that the expander disassembles in the mouth.

A further object of the present finding is to provide a method for the assembly of a rapid palatal expander which is easy to obtain, even if providing such expander with an end stop in the opening.

These objects and still others are all achieved by the rapid palatal expander, object of the present invention, which comprises a rod-shaped actuator element with main extension in a longitudinal direction Y, provided with a drive head arranged in a substantially median position thereof, and with two stems which are extended aligned in opposite directions from the drive head, with threads in opposite senses provided; a first and a second main body provided with corresponding opposite first and second front face with respective aligned female threads obtained, each engaged by a threaded stem of the actuator element; guide means for guiding the simultaneous movement of the main bodies along the longitudinal direction Y following the rotation of the drive head.

According to the idea underlying the present invention, the rapid palatal expander is characterized in that the guide means comprise: a first pair of rods, which are fixed in a single body with the first main body, from whose first front face such rods are extended parallel to each other towards the second main body; a second pair of rods, which are fixed in a single body with the second main body, from whose second front face such rods are extended parallel to each other towards the first main body; the first and the second pairs of rods being at least partially slidably and mutually engaged with each other in a form relationship in order to guide the movement of the first and the second main body with a single degree of freedom in the aforesaid longitudinal direction Y.

BRIEF DESCRIPTION OF THE DRAWINGS

The technical characteristics of the finding, according to the aforesaid objects, are clearly seen in the contents of the below-reported claims and the advantages thereof will be clearer from the following detailed description, made with reference to the enclosed drawings which represent several merely exemplifying and non-limiting embodiments thereof, in which:

FIG. 5 shows a top view of the rapid palatal expander according to the present invention, in closed position and in accordance with a first embodiment variant, and with the arms for transmitting the pressure to the teeth anchorage bands omitted;

FIG. 6 shows a side view in section of the expander of FIG. 5, carried out along the line VI-VI of FIG. 5;

FIG. 12 shows a plan view of the expander of FIG. 10 and with some parts removed in order to better illustrate other parts;

FIGS. 13 and 14 show a detail of the expander of FIG. 10 relative to an actuator element and with a clip respectively in disassembled and assembled position;

FIG. 15 shows a perspective view of the rapid palatal expander according to the present invention, in closed position, in accordance with a third embodiment variant and with the arms for transmitting the pressure to the teeth anchorage bands omitted;

FIG. 16 shows a top view of the expander of FIG. 15;

FIG. 17 shows a side view in section of the expander of FIG. 16, carried out along the line XVII-XVII of FIG. 16;

DETAILED DESCRIPTION OF A PREFERRED EMBODIMENT

Figure 1:
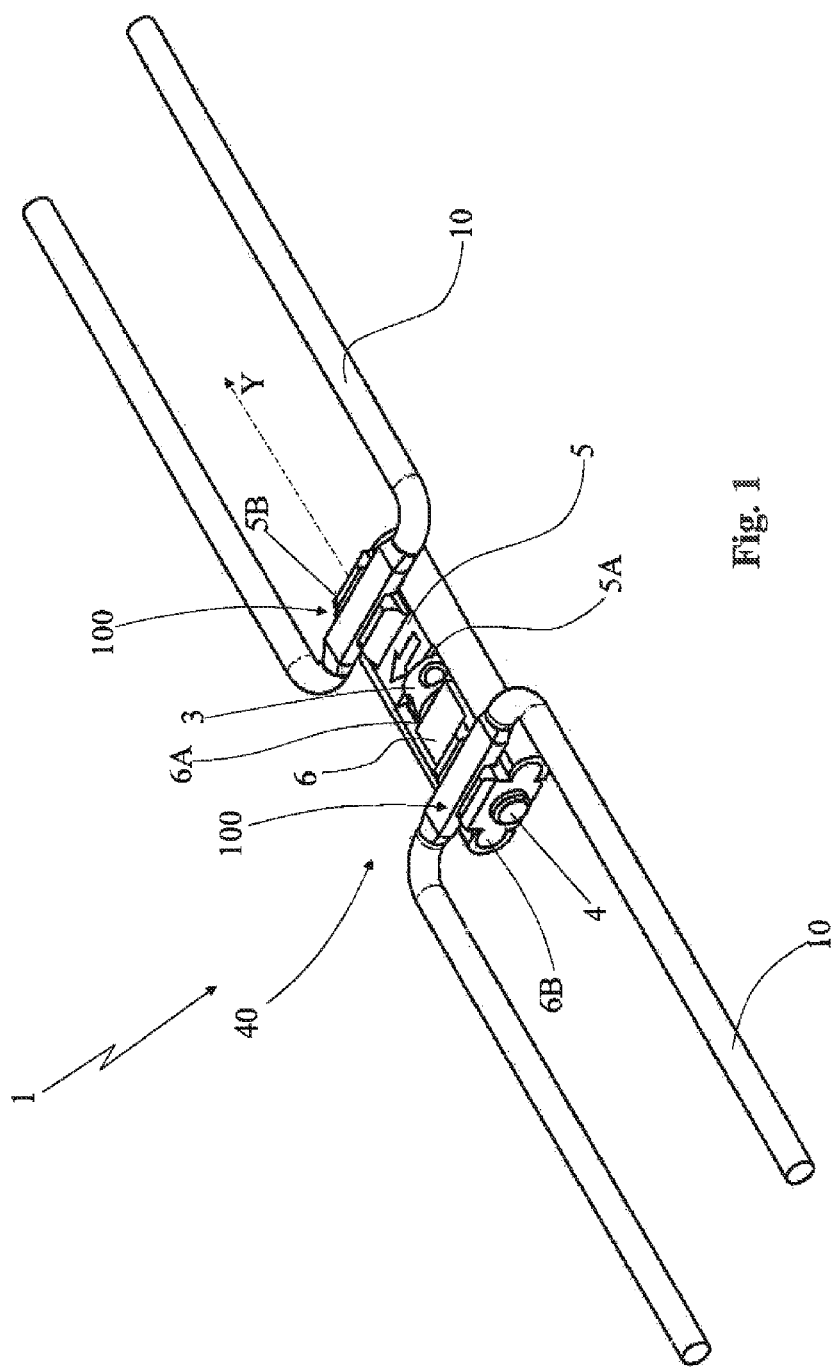
FIG. 1 shows a general perspective view of one embodiment of the rapid palatal expander according to the present invention.
Figure 2:
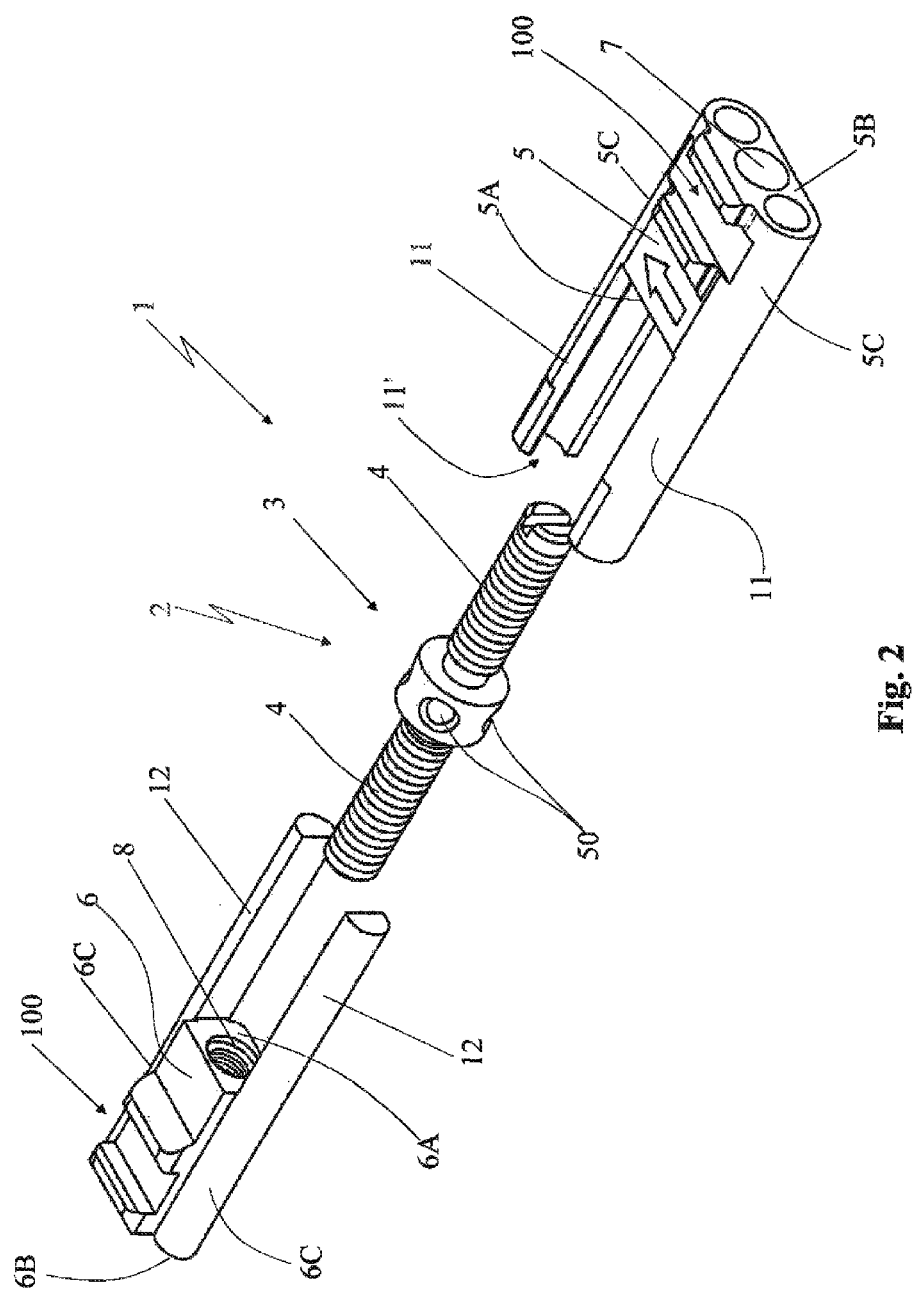
FIG. 2 shows an exploded perspective view of the expander of FIG. 1 with some parts removed (arms for transmitting the pressure to the teeth anchorage bands) in order to better illustrate other parts.
Figure 3:
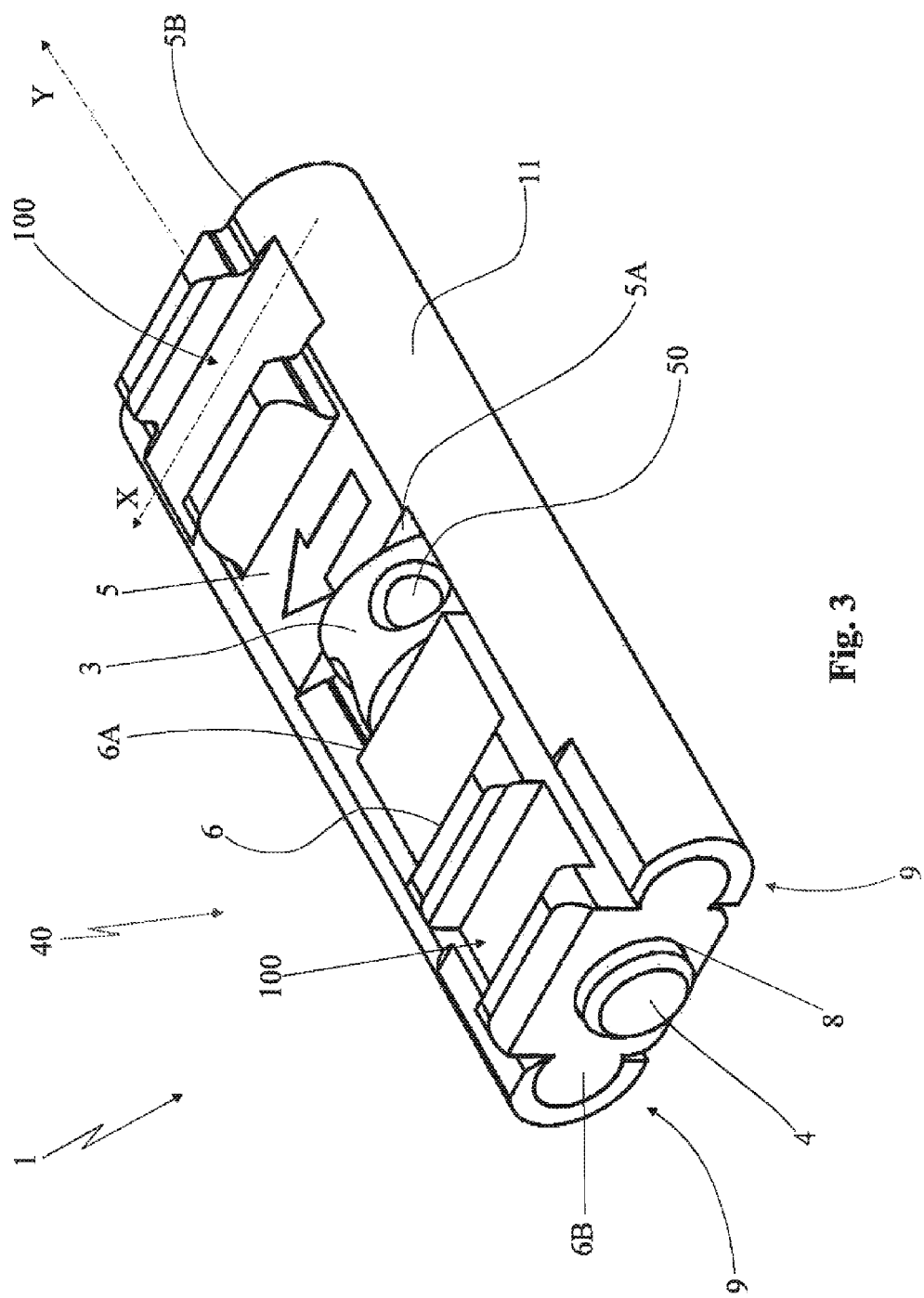
FIGS. 3 and 4 show the assembled expander of FIG. 2, respectively in a closed (or minimum expansion) position and in an open (or maximum expansion) position.
Figure 4:
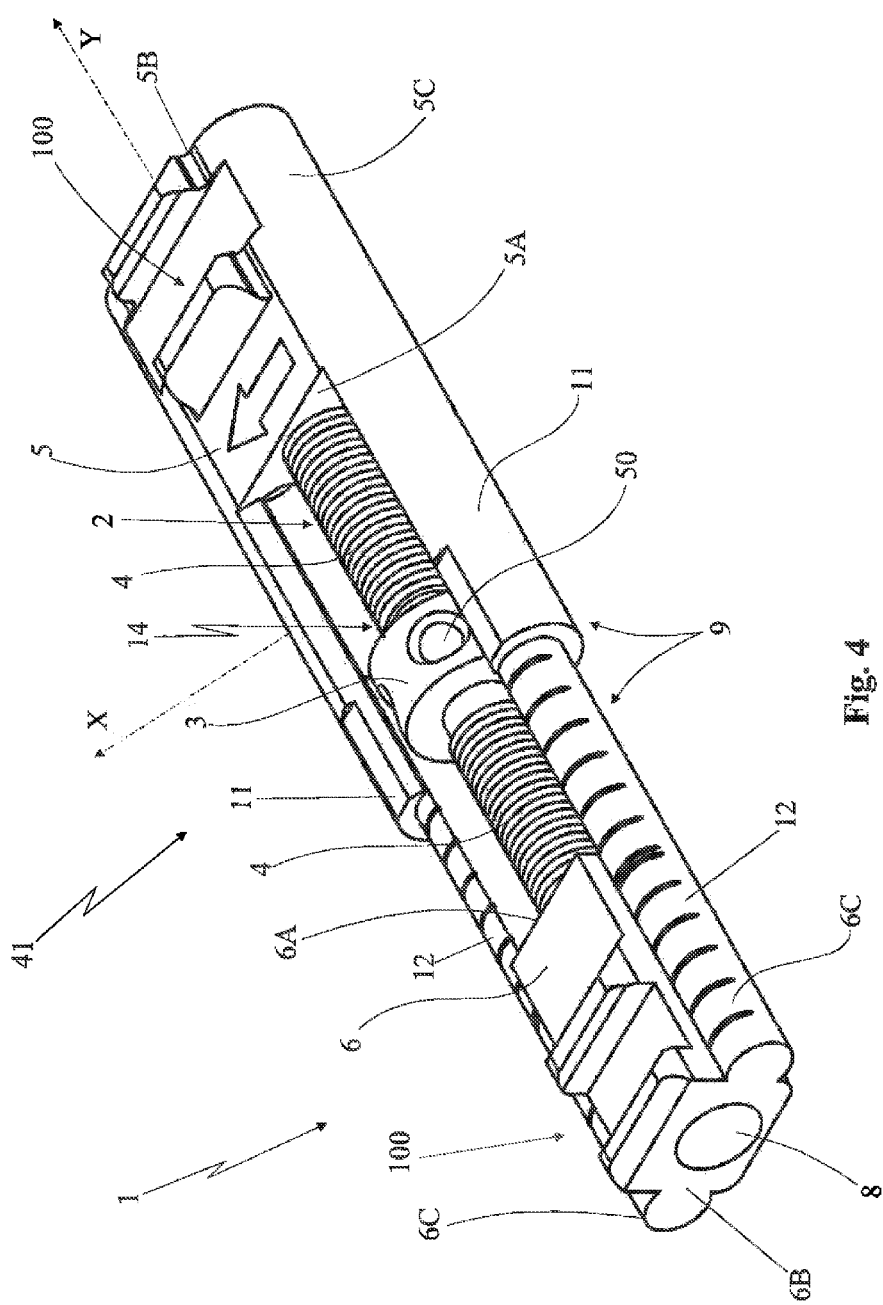
Figure 7:
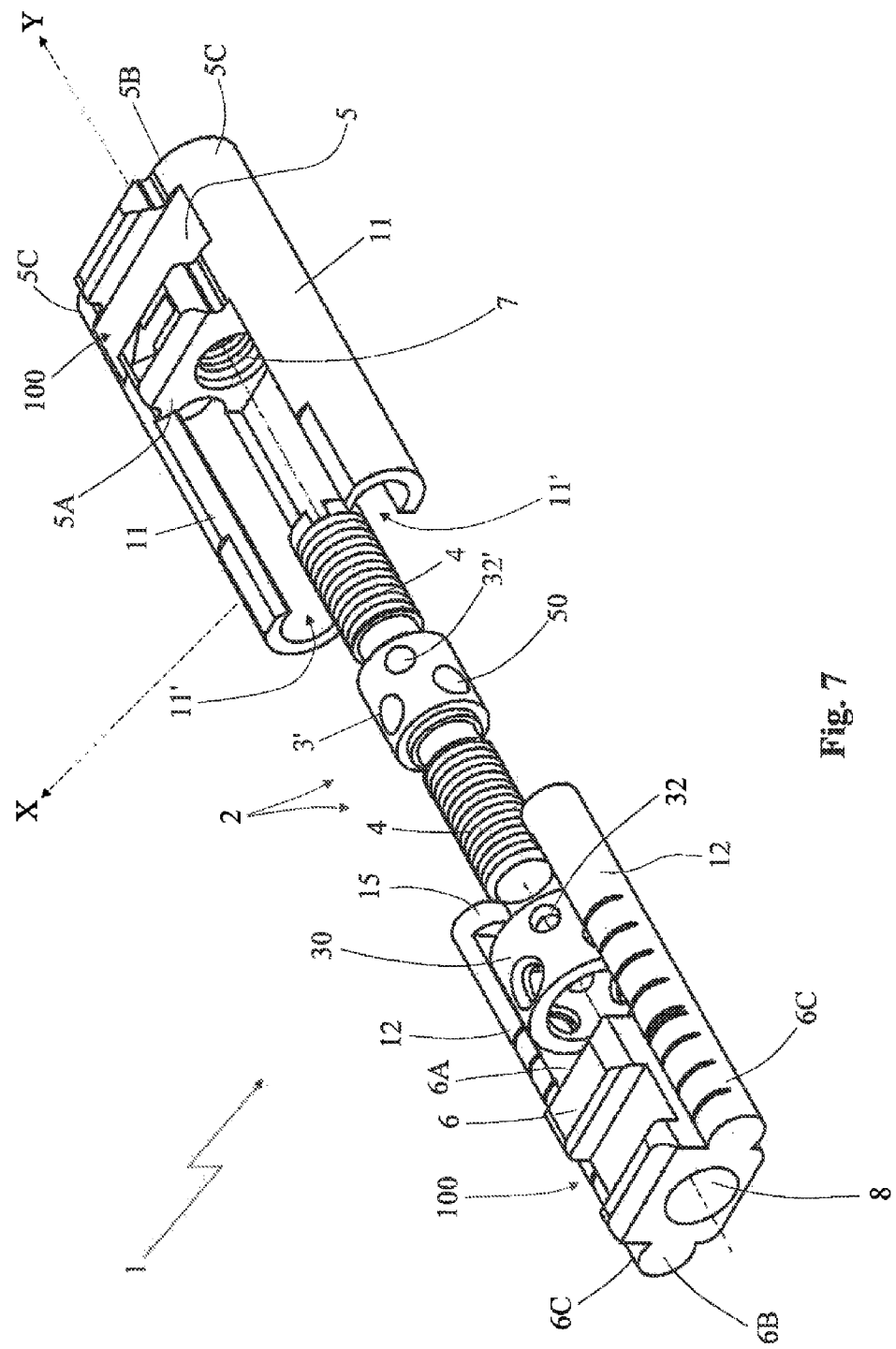
FIG. 7 shows an exploded perspective view of the expander of FIG. 5 with some parts removed (the arms for transmitting the pressure to the teeth thrust bands) in order to better illustrate other parts.
Figure 8:
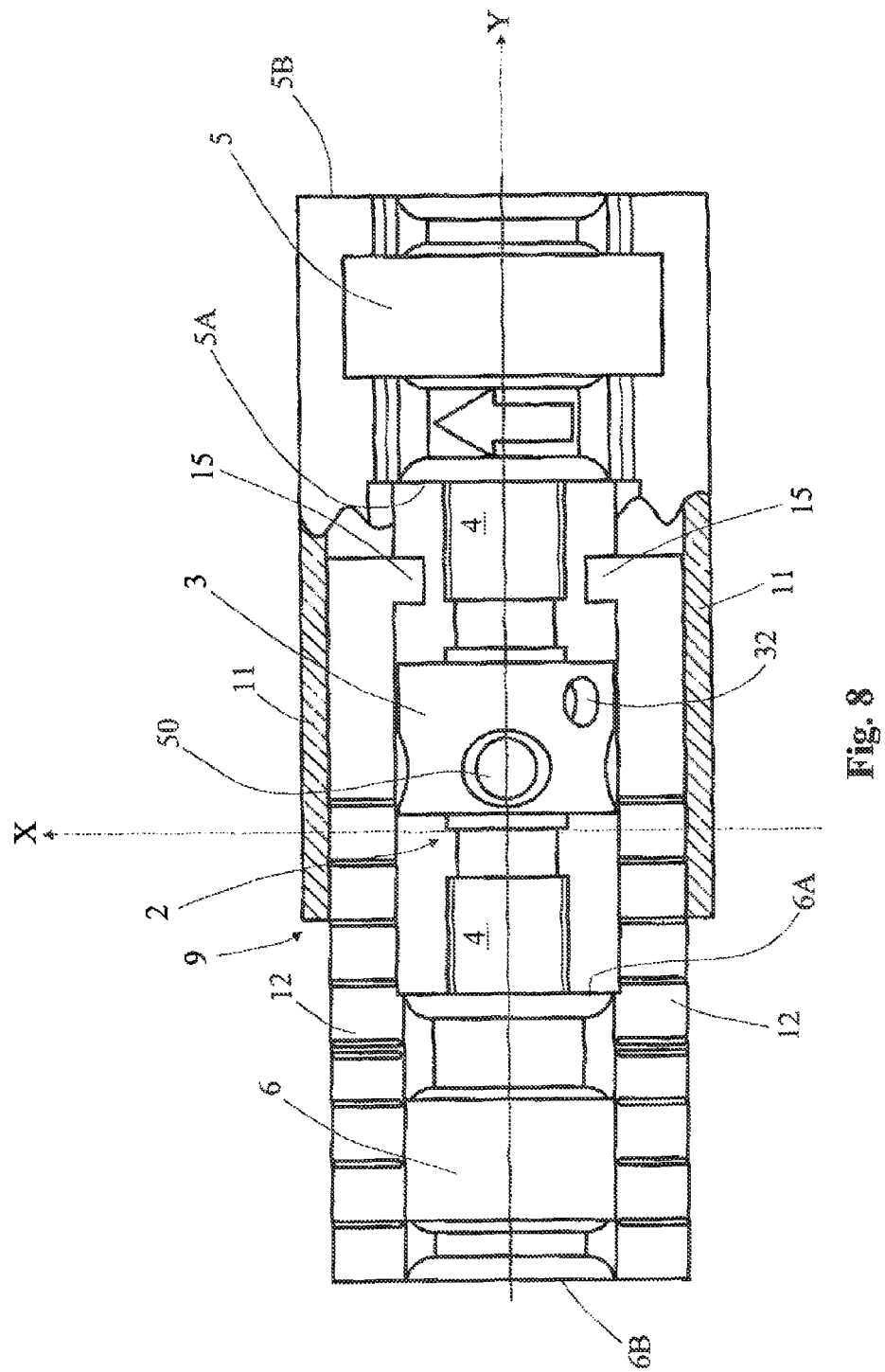
FIG. 8 shows a plan view of the expander of FIG. 5, in nearly open position, and with some details relative to a female pair of rods in section according a plane parallel to the position of the same rods, in order to better illustrate the presence of their nose sections.
Figure 9:
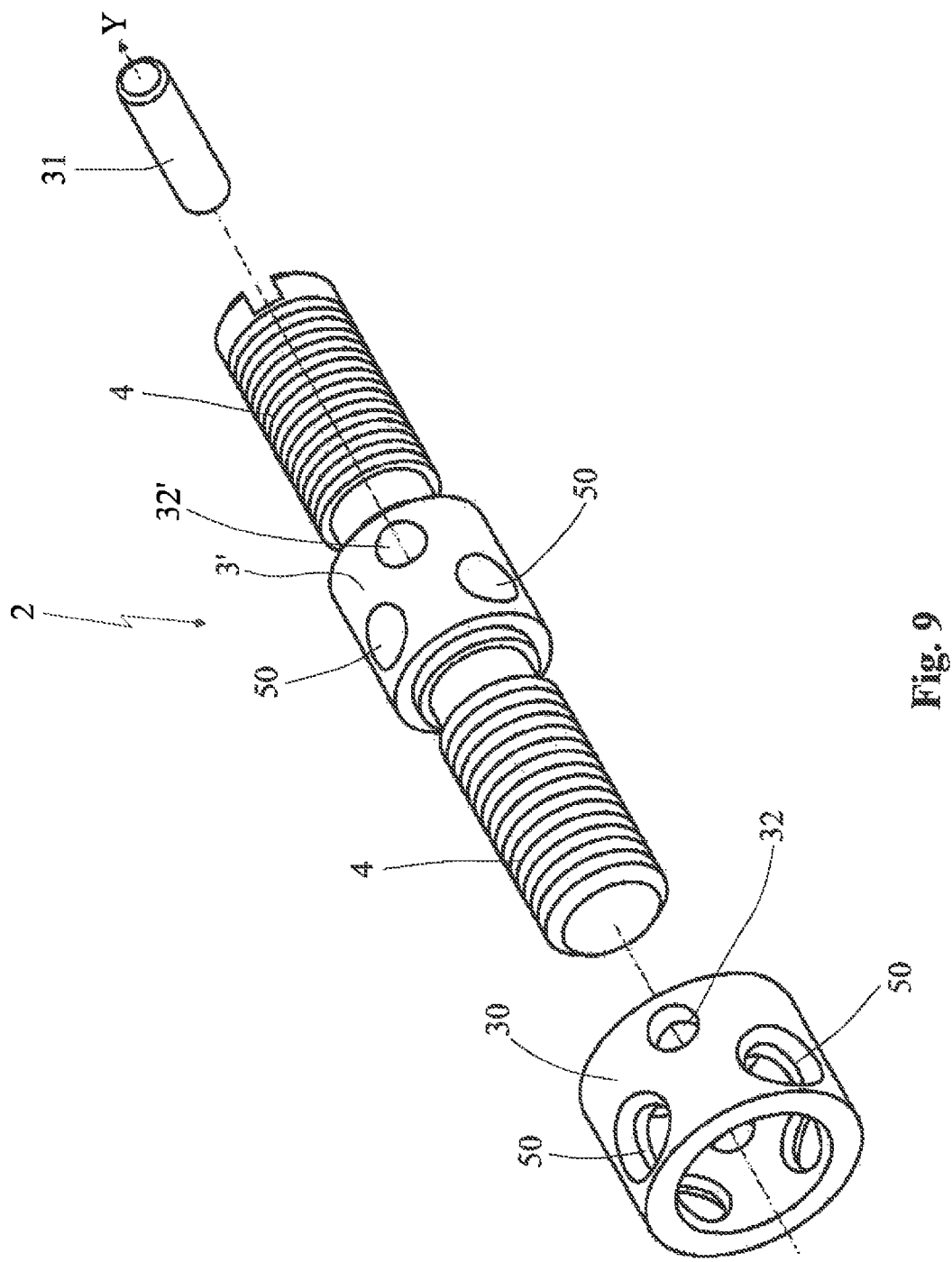
FIG. 9 shows a perspective view of an enlarged detail of the expander of FIG. 5 relative to an actuator element.
Figure 10:
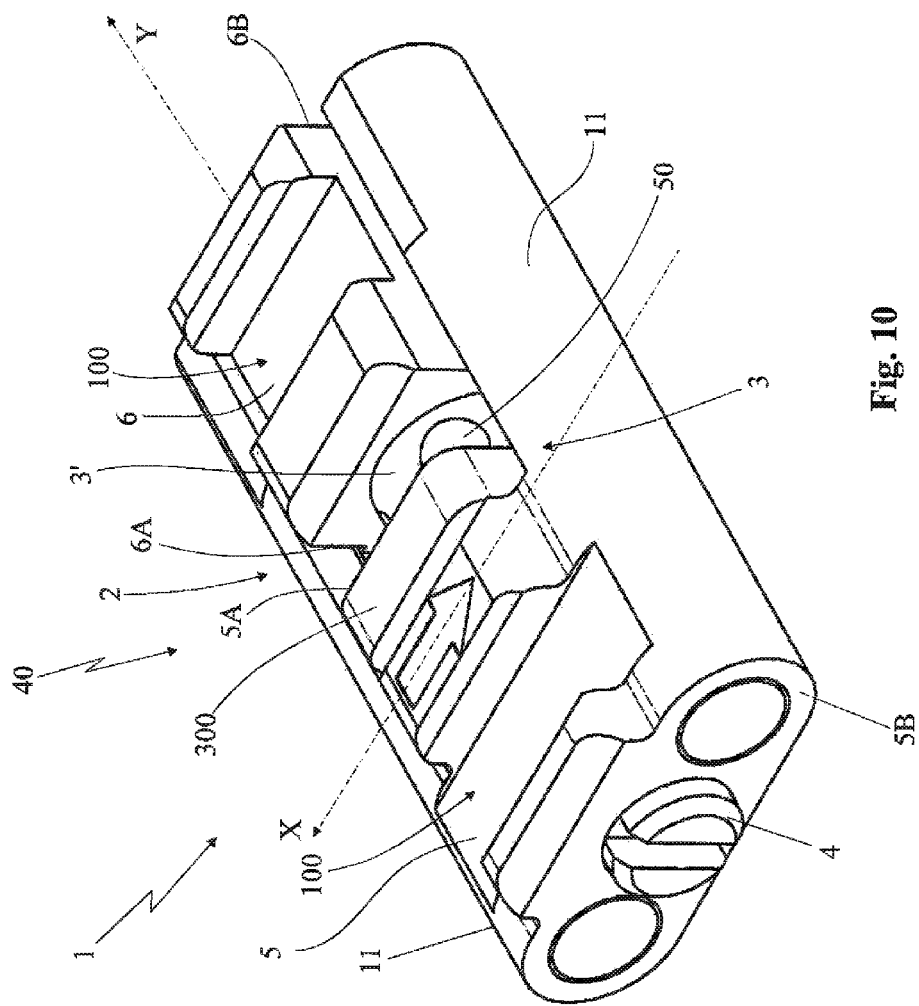
FIGS. 10, 11 show two perspective views of the rapid palatal expander according to the present invention, respectively in closed position and open position, in accordance with a second embodiment variant and with the arms for transmitting the pressure to the teeth anchorage bands omitted.
Figure 11:
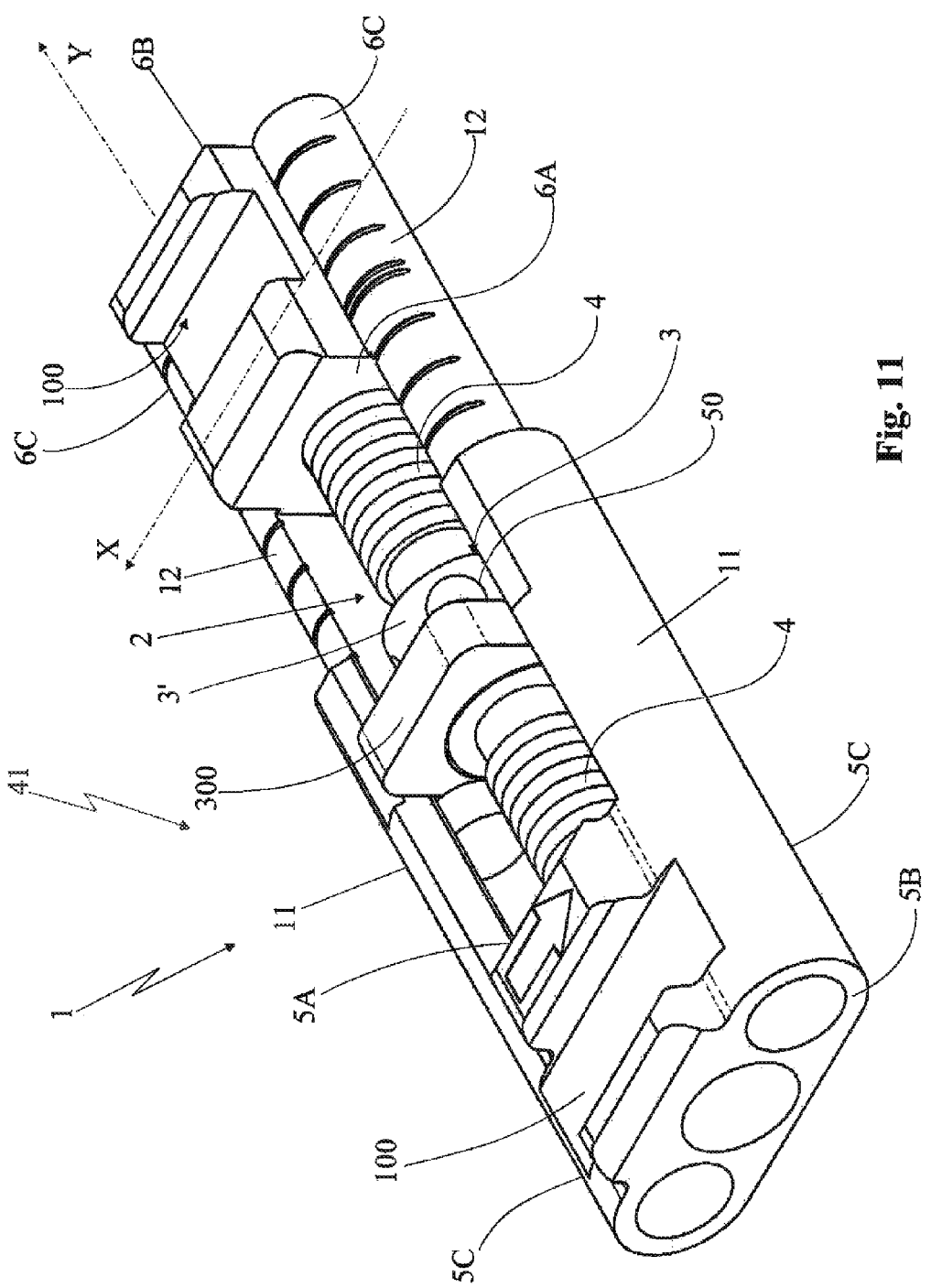
Figure 18:
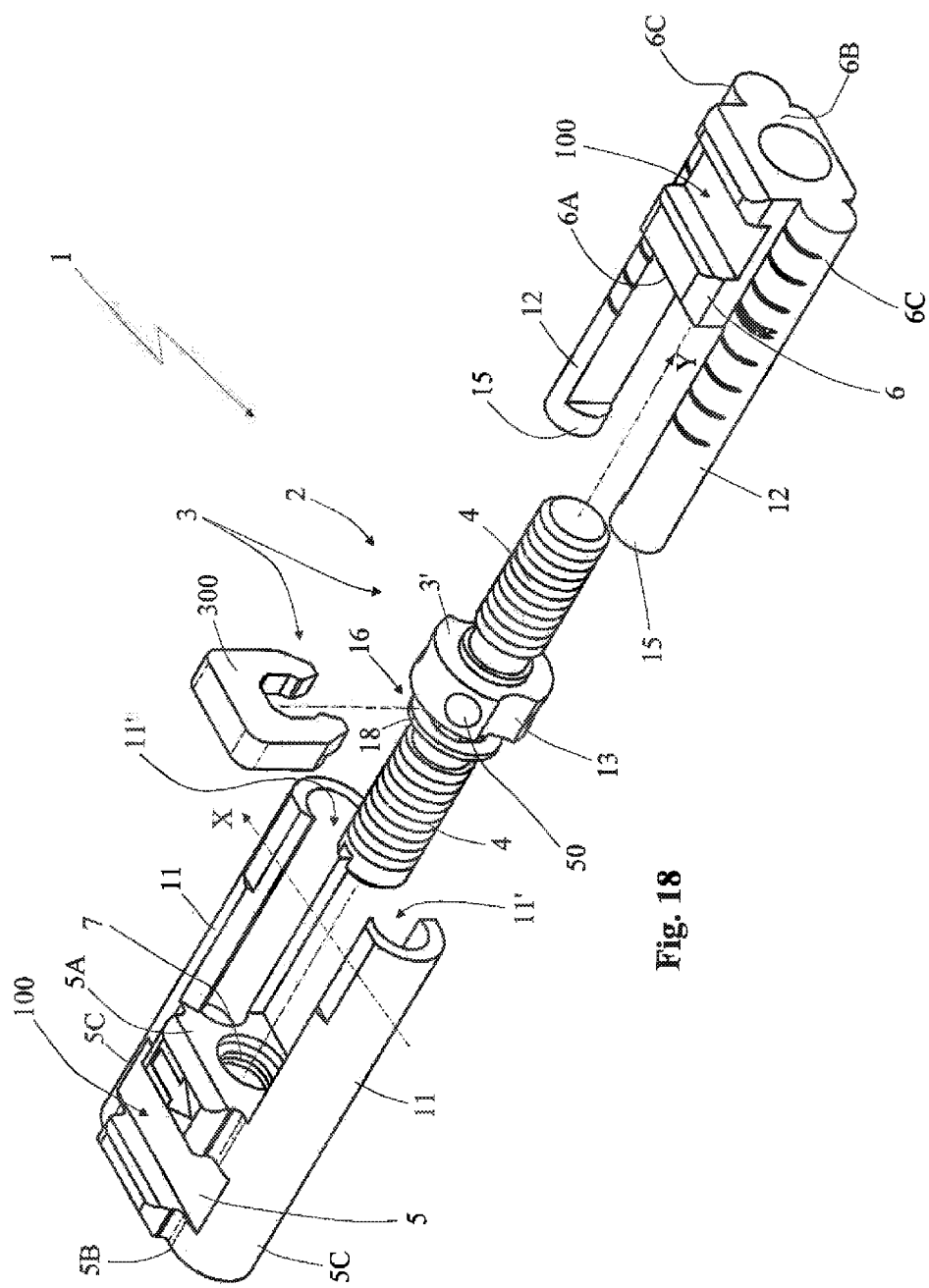
FIG. 18 shows an exploded perspective view of the expander of FIG. 15.
Figure 19:
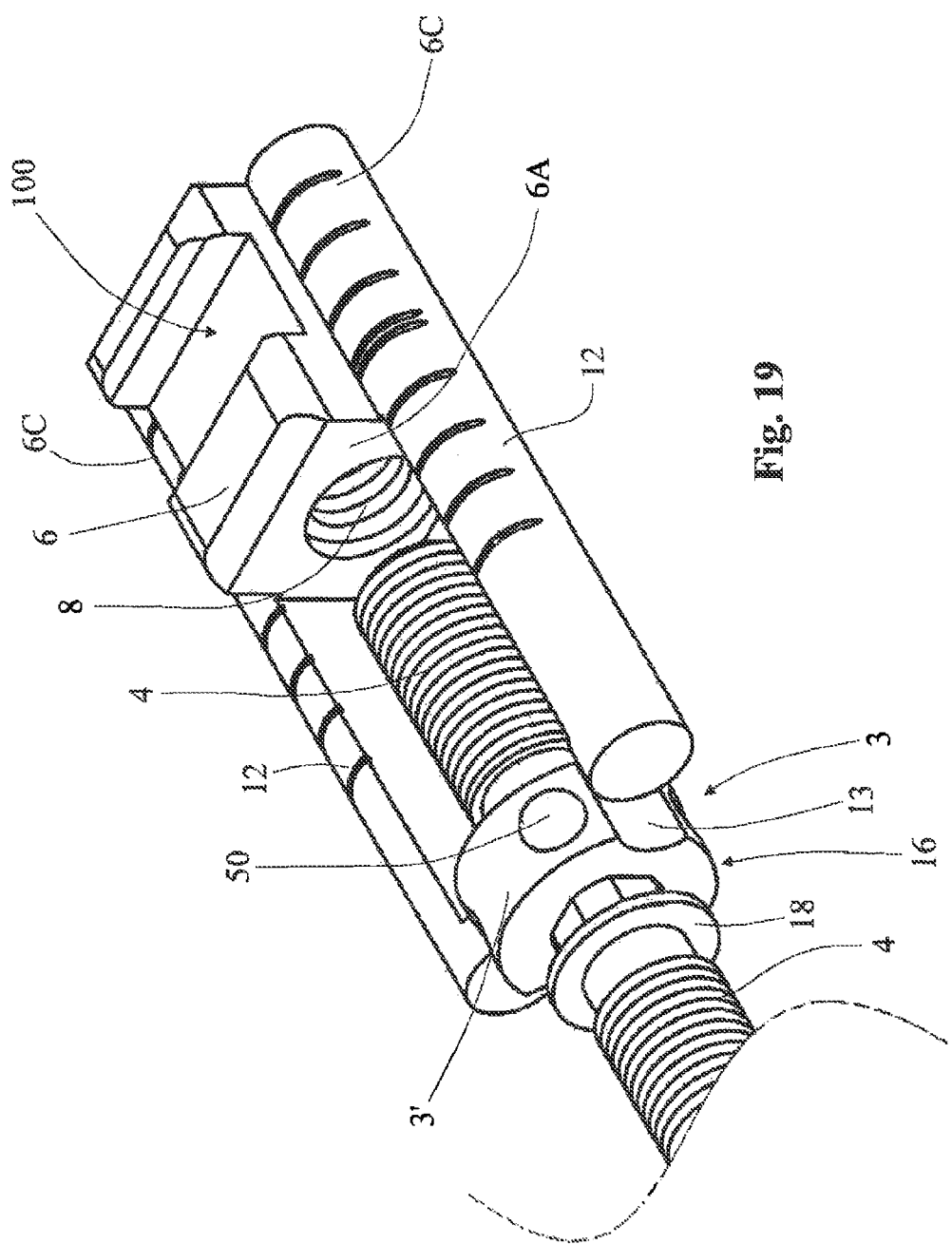
FIG. 19 shows a perspective view of a detail of the expander of FIG. 15, relative to the passage of the male rods in outlets of the drive bead during the step for the assembly of the expander.

With reference to the set of drawings, the rapid palatal expander that is the object of the present invention has been indicated in its entirety with the reference number 1.

The rapid palatal expander 1, according to the present invention, is intended to be employed in a per se conventional manner in the orthodontics field for the pathological correction of a hypoplasia of the upper jaw, as already indicated above in the explanation of the field of application of the present finding.

It comprises an actuator element 2 with rod-shaped form, having a main extension in a longitudinal direction Y. Such element is provided with a drive head 3, central or placed in a substantially median position with respect to the longitudinal extension thereof, and with two stems 4 which are extended aligned with each other along such longitudinal direction Y, in opposite directions starting from the aforesaid drive head 3. The two stems 4 are provided with two threads oriented in opposite senses such that there is simultaneous screwing and unscrewing for both the stems 4 with respect to corresponding female threads on which they are engaged as described hereinbelow.

The rapid palatal expander 1 also comprises, in a per se known manner, a first main body 5 and a second main body 6 provided with corresponding first front face 5A and second front face 6A, which are arranged parallel and facing each other.

Respective female threads 7 and 8 are obtained on such faces; such threads are aligned with each other, and each is engaged by one of the two threaded stems 4 of the actuator element 2.

Guide means 9 are then provided for guiding the simultaneous movement of the two main bodies 5, 6 in an advancement direction thereof which coincides with the longitudinal extension direction Y of the actuator element 2. The two main bodies 5, 6, being engaged to the stems 4 with opposite threads of a same actuator element 2, are moved closer to or further apart from each other following the rotation of the drive head 3, always in a synchronized manner in the same direction Y but in opposite senses.

The two main bodies 5 and 6 are mechanically fixed to two or more rigid arms 10 which are extended in substantially opposite directions and which are intended to interact, by means of teeth anchorage bands (e.g. molar bands) or other mechanical elements, with corresponding opposite portions of the dental arch.

The arms 10 are generally rigidly fixed in provided seats 100 of the main bodies 5, 6 by means of welding.

Operatively, once the rapid palatal expander 1 is installed in the mouth of the patient—with the bands gripping on the teeth in order to transmit thereto, through the arms 10, the thrust pressure of the main bodies 5, 6 kept spaced by the action of the actuator 2—one proceeds day after day to support the widening movement set by the actuator element 2 by means of the arms 10 to the rows of teeth of the dental arch of the patient, rotating the drive head 3 of the actuator 2 by a predefined angle, usually an angle of 90 degrees each day or by a multiple of 90 degrees each day.

According to the idea underlying the present invention, the guide means 9 comprise at least one first rod 11, which is fixed in a single body with the first main body 5, from whose first front face 5A such rod is extended towards the second main body 6, and at least one second rod 12, which is fixed in a single body with the second main body 6, from whose second front face 6A such rod is extended towards the first main body 5.

The two rods 11 and 12 are at least partially mutually engaged with each other in a form relationship in order to guide the movement of the two main bodies 5, 6 with a single degree of freedom in the aforesaid longitudinal direction Y.

In accordance with a preferred embodiment of the present invention to which reference will be made hereinbelow, the guide means advantageously comprise not a single rod associated with the relative main body but rather a pair of rods or more clearly: a first pair of rods 11, which are rigidly fixed to the first main body 5, are obtained in a single body with the latter, and they are extended parallel to each other towards the second main body 6 starting at least from the first front face 5A, and a second pair of rods 12, which are in turn rigidly fixed to the second main body 6, are obtained in a single body with the latter and they are extended parallel to each other towards the first main body 5 starting at least from the second face 6A.

Of course, without departing from the protective scope of the present invention, the following description made with reference to two pairs of rods 11, 12 must also be intended as extended to main bodies 5, 6 with a single rod 11, 12 associated for each main body 5, 6.

More in detail, the two pairs of rods are telescopically inserted in each other. For example, the first pair of rods 11 are of female type, each with longitudinal cavity 11' at whose interior the rods of male type of the second pair of rods 12 are inserted in a form relationship; such male rods have section slightly less than the female rods 11 in order to slidably enter into the longitudinal cavities 11' of the female rods 11 with minimum clearance.

Preferably, the latter rods of female type 11 are transversely placed more external than the rods of male type 11 in the transverse direction X orthogonal to the advancement direction Y of the main bodies 5, 6.

In addition, the rods of female type 11 preferably have C-shaped cross section with facing longitudinal internal concavities. Advantageously, the concavities of the female rods 11 are circumferentially extended for an angle greater than 180° in order to retain constrained the male rods 12 at their interior, also with respect to shifting transverse to the advancement direction Y of the main bodies 5, 6 and lying in the plane of the rods 11, 12.

The drive head 3 is advantageously cylindrical and provided, in a per se already known manner, with a plurality of first holes 50 with radial extension, circumferentially arranged in an equidistant manner, within which a key (not illustrated since it is of per se known type) can be coupled in order to impart a rotation to the head 3 aimed to adjust the compression of the expander 1 through its arms 10 of the palatal arch. Preferably, there are four such first holes 50 angularly arranged at 90 degrees from each other.

The drive head 3 is housed in a seat 14 delimited in a direction transverse to the extension direction Y, between the mutually engaged rods of the two pairs of rods 11, 12 (i.e. in particular between one coupling of male/female rods and the other coupling of coupling of male/female rods), and in the extension direction Y, between the first and second front face 5A, 6A of the two main bodies 5, 6.

The rods of the two pairs of rods 11, 12 project from the relative first and second front face 5A, 6A but are preferably also extended on the two lateral flanks of the two main bodies 5, 6 indicated with reference numbers 5C and 6C. More particularly, the two female rods 11 define two corresponding tubular cavities at the two flanks of the first main body 5 whereas the two male rods 12 define two corresponding rails or lobes with convexities directed transversely outward, and counter-shaped with respect to the facing concavities directed towards the interior of the female rods 11.

The two main bodies 5 and 6 are controlled to be moved by the rotation of the drive head 3 between a closed or minimum expansion position 40, in which the rods of the pair of male rods 12 are substantially entirely inserted in the pair of female rods 11, given that the end stop is for example determined by the abutment of the two front faces 5A and 6A against the drive head 3, and an open or maximum expansion position 41, in which the rods of the pair of male rods 12 penetrate the cavities of the female rods 11 only for a limited terminal portion thereof and the end stop is in this case defined as better specified below in accordance with different embodiments.

Preferably, in the closed position 40, the free ends of the female rods 11 and male rods 12 arrive in proximity to, or even flush with, the first and second rear face 6B, 5B of the two main bodies 6, 5, respectively.

In accordance with an advantageous characteristic of the present invention illustrated in FIGS. 5-19, the end stop in the opening of the palatal expander 1 is obtained by means of at least one nose section 15, arranged at a free end of at least one rod of at least one of the two pairs of rods 11, 12 and projecting towards the other rod of the same pair of rods 11, 12, so as to abut against an enlarged portion of the drive head 3.

More in detail, the nose section 15 is obtained at the end of at least one rod of the more internal pair of rods which preferably, in accordance with the embodiment illustrated in the enclosed figures, is constituted by the pair of male rods 12.

Preferably, two nose sections 15 are provided, directed facing each other at the free ends of both the rods of the pair of male rods 12, in order to balance the end stop stresses with respect to a median plane of the expander 1 passing through the extension axis Y of the actuator element 2 and orthogonal to the plane of the rods 11, 12.

The abovementioned nose sections 15 are obtained in a single body with the relative pair of male rods 12 and with the relative second main body 6. Otherwise, the nose sections 15 can be obtained at the free ends of the pair of female rods 11, as can be seen in the embodiment reported in FIG. 20.

In order to allow an easy assembly of the palatal expander 1, object of the present invention, without having to bend the male rods 12 (provided with considerable rigidity) in order to allow the passage of the drive head 3, the latter is preferably composed of a central core 3' with width L less than the minimum distance D that lies between the more internal rods of the two pairs of rods 11, 12; i.e. in accordance with the particular embodiment illustrated in the enclosed figures, less than the reduced distance D that lies between the nose sections 15 provided at the free ends of the two male rods 12. In this manner, the actuator element 2 thus obtained with the single core 3' is in all parts thereof narrower than the distance between the internal rods of male type 12, which laterally define the seat 14, and such actuator element 2 can easily be inserted in assembly step between the two main bodies 5 and 6 and screwed thereto.

Subsequently, an enlarged portion 30, 300 of the drive head 3 is mechanically associated with the core 3', which interferes with the nose sections 15 (having width greater than D) in order to obtain the end stop in the opening of the expander 1. Of course, the enlarged portion 30, 300 is associated with the central core 3', only after the latter has been moved via the screwing of the stems 4 from an initial position adjacent to the nose sections 15 to a position no longer facing the nose sections 15.

In order to enlarge the core 3', with substantially cylindrical form, various embodiments are provided for.

In accordance with the embodiment of FIGS. 5-9, the enlarged portion has the form of an annular ring indicated with 30, which is mechanically peripherally associable to the core 3', e.g. by means of a pin 31 which is forcibly inserted in a radial hole 32 obtained with a through opening made on the ring 30 and with a hole 32' aligned with the opening provided on the core 3'.

Advantageously, the first holes 50 mentioned above for the coupling of the key—which causes the rotation of the drive head 3—are also obtained with a through opening made in the ring 30 and with a hole aligned with the opening provided in the core 3'.

In accordance with a different embodiment of the present invention illustrated in FIGS. 10-14, the cylindrical core 3' has associated—in particular flanking one of the stems 4 in the connector section—a groove 16, in which a clip 300 is engageable, in particular with elastic snap coupling. Such clip 300 is susceptible to interfere with the nose sections 15 in order to obtain the aforesaid end stop.

Otherwise, the end stop in the opening can be obtained from the same core 3' of the drive head 3, which will annularly define the portion projecting beyond the reduced distance D with its peripheral edge, in order to interfere with the nose sections 15. At the same time, in accordance with this embodiment illustrated in FIGS. 15-19, the core 3' also has two longitudinal external lateral outlets 13 for allowing, in assembly step, the actuator element 2 to pass with the head 3 through the nose sections 15. The clip 300 in this case carries out the function of closing the aforesaid lateral outlets 13 once the head 3 has been screwed and positioned beyond the nose sections 15, in order to prevent the drive head 3 in completely open position from being situated at the aforesaid outlets 13, causing the detachment of the actuator element 2 from the main bodies 5, 6 and in substance the breaking apart of the expander 1.

Advantageously, the clip 300 is in any case engaged with its lateral walls between the opposite faces of the more internal pair of rods (the male rods 12 in accordance with the enclosed figures), such that it cannot rotate around the axis Y during the movement of the main bodies 5, 6 and of the rods 11, 12 therewith. For such purpose, the clip 300 has a square form with the parallel lateral walls susceptible to sliding on the internal face of the male rods 12.

Preferably, the groove 16 is placed on one side of the drive head 3; the groove 16 is delimited on one side, towards the median portion of the actuator element 2, by the same drive head 3 (i.e. by its core 3') and on the other side, towards the threaded stem 4, by an annular flange 18 fixed to the same actuator element 2, which prevents the clip 300 from being axially moved along the extension direction Y of the same actuator element 2.

Also forming an object of the present invention is a method for the assembly of the above-described rapid palatal expander 1; for descriptive ease, the numeric references and the nomenclature used above will be maintained hereinbelow.

The aforesaid method is employed for the palatal expander 1 embodiments provided with projecting nose section 15, so that it is necessary to provide for a sequence of operations aimed first for the screwing of the actuator element 2 assembled in an incomplete manner and not interfering with the nose section 15, and then subsequently aimed to determine an enlargement of the drive head 3, in order to define the end stop in the opening in interference with the nose section 15.

Therefore, the method provides for the obtainment of the drive head 3 in two parts, as described above, including a core 3' and an enlarged portion 30, 300, joinable to the core 3' in order to increase the size thereof.

According to the idea underlying the present invention, the assembly method thus provides for a step for inserting the actuator element 2, with the drive head 3 provided with the single core 3', in the seat 14 between the opposite front faces 5A and 6A of the two main bodies 5, 6, with the stems 4 aligned with the female threads 7 and 8; then, there is a step for the at least partial screwing of the actuator element 2 with relative sliding of the first and second rods 11, 12 and consequent positioning of the head 3 outside the bulk of the nose section 15 or the two nose sections 15.

At this point, a step is provided for associating the enlarged portion 30, 300 of the head 3 with the core 3', thus to restore a bulk of the head 3 that prevents the actuator element 2 being unscrewed from returning to separate the two main bodies 5, 6.

Figure 20:
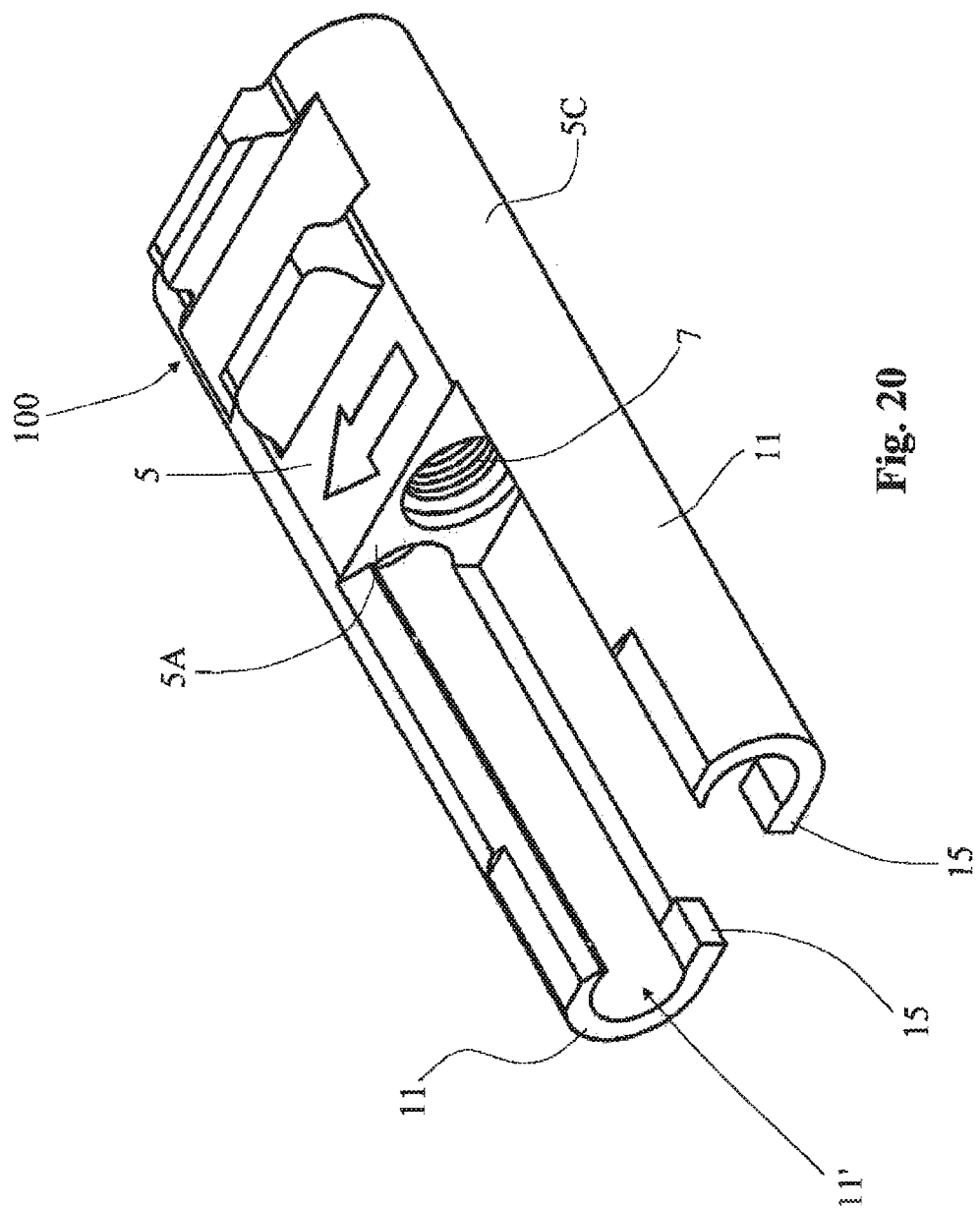
FIG. 20 shows a perspective view of a detail of the rapid palatal expander according to the present invention in accordance with a fourth embodiment variant relative to a main body with female rods provided with projecting nose sections.

The aforesaid association step can provide for, in the case of the enlarged portion constituted by a ring 30, the previous arrangement of the same ring 30 between the female thread 7 or 8 of the main body 5 or 6 whose rods are provided with nose sections 15 (i.e. between the female thread 8 of the main body 6 having male rods 12 with nose sections 15, with reference to the embodiment of FIGS. 5-9; otherwise, between the female thread 7 of the main body 5 having female rods 11 with nose sections 15 with reference to the embodiment of FIG. 20) and a stem 4 so as to allow the latter to be inserted inside the ring 30, during the insertion step of the actuator element 2, and then a step for moving the ring 30 along the stem up to the external surface of the core 3' in order to then actuate the subsequent fixing thereof on such external surface for example by means of a pin 31.

Otherwise, in the case in which the enlarged portion is constituted by a clip 300, the aforesaid association step can provide for the simple coupling, subsequent to the screwing step, of the clip 300 in the groove 16 placed alongside the core 3' of the head 3.

Of course, the rapid palatal expander can also assume, in the practical achievement thereof, shapes and configurations different from that illustrated above, without departing from the present protective scope.

In addition, all details can be substituted by technically equivalent elements, and the size, shapes and materials used can be of any type as required.

The invention claimed is:

1. Rapid palatal expander which comprises:
   a rod-shaped actuator element (2) with a main extension in a longitudinal direction (Y), provided with a drive head (3) arranged in a substantially median position of the rod-shaped actuator, and with two stems (4) which are aligned and extend in opposite directions from said drive head (3), each of said stems configured with threads in opposite direction with respect to each other,
   a first and a second main body (5, 6) provided with a respective corresponding opposite first and second front face (5A, 6A), the first and second front faces are configured with respective female threads (7, 8), such that each said first and second front face is engaged by one of said stems (4) configured with threads of said actuator element (2);
   a guide means (9) for guiding a simultaneous movement of said first and second main bodies (5, 6) along said longitudinal direction (Y) following rotation of said drive head (3);
   characterized in that said guide means (9) comprise:
   a first pair of rods (11) fixed in a single body with said first main body (5) and extending from the first front face (5A), the first pair of rods extend parallel to each other and extend towards said second main body (6);
   a second pair of rods (12) fixed in a single body with said second main body (6) and extending from the second front face (6A), the second pair of rods extend parallel to each other and extend towards said first main body (5);
   wherein said first and said second pair of rods (11, 12) are at least partially slidably and mutually engaged with each other in a form relationship in order to guide the movement of said first and second main body (5, 6) with a single degree of freedom in said longitudinal direction (Y);
   wherein at least one free end of at least one rod of at least one of said first and second pairs of rods (11, 12) is provided with a nose section (15) that is internally projecting towards the other rod of said pair of rods (11, 12) of the same main body (5, 6), which transversely defines a reduced minimum distance (D) between said pair of rods; said nose selection (15) being susceptible to abut against an enlarged portion (30, 300) of said drive head (3) in order to define an end stop in an opening of the expander (1).

2. Rapid palatal expander according to claim 1, characterized in that one of said first and second pair of rods (11, 12) are arranged more internally towards said rod-shaped actuator element (2) than the other said pair of rods (11); said at least one nose section (15) being disposed on said at least one rod of the said more internal pair of rods (11, 12), so as to define said reduced distance (D) therebetween.

3. Rapid palatal expander according to claim 1, characterized in that said drive head (3) includes a central core (3') and said enlarged portion (30, 300) is a removable element mechanically associable to said core (3');
   such that said central core (3') when not mechanically associated with said enlarged portion (30, 300) has a width (L) so as to be capable of translating along said extension direction (Y) without interfering with said nose section (15),
   said drive head (3), when said central core (3') is mechanically associated with said enlarged portion (30, 300), has a width (L) greater than said reduced distance (D) so as to be capable of interfering with said nose section (15) along said extension direction (Y) in order to obtain said end stop.

4. Rapid palatal expander according to claim 3, characterized in that said core (3') has a cylindrical form and said enlarged portion has an annular ring form (30), which is mechanically fixable on an external peripheral surface of said core (3').

5. Rapid palatal expander according to claim 3, characterized in that said core (3') has a groove (16), and said enlarged portion is configured as a clip mechanically engageable with said groove so as to be capable of interfering with said nose section (15) in order to obtain said end stop.

6. Rapid palatal expander according to claim 1, characterized in that said drive head (3) comprises a central core (3') provided with said enlarged portion capable of interfering with said nose section (15) along said extension direction (Y), in order to obtain said end stop, said central core (3") being also provided with at least one longitudinal outlet (13) capable of being crossed by said at least one nose section (15), said central core (3') having a groove (16) associated therewith, in which said enlarged portion in form of a clip (300) is mechanically engageable to close said longitudinal outlet (13); said nose section (15) being capable of abutting against said drive head (3) or said clip (300) in order to define said end stop in the opening of the expander (1).

\* \* \* \* \*